United States Patent
Backues et al.

(10) Patent No.: US 10,481,088 B2
(45) Date of Patent: Nov. 19, 2019

(54) AUTOMATIC DETERMINATION OF FOURIER HARMONIC ORDER FOR COMPUTATION OF SPECTRAL INFORMATION FOR DIFFRACTION STRUCTURES

(71) Applicants: Mark Backues, San Diego, CA (US); Paul Aoyagi, Sunnyvale, CA (US); Leonid Poslavsky, Belmont, CA (US)

(72) Inventors: Mark Backues, San Diego, CA (US); Paul Aoyagi, Sunnyvale, CA (US); Leonid Poslavsky, Belmont, CA (US)

(73) Assignee: KLA-TENCOR CORPORATION, Milpitas, CA (US)

( * ) Notice: Subject to any disclaimer, the term of this patent is extended or adjusted under 35 U.S.C. 154(b) by 1248 days.

(21) Appl. No.: 14/293,809

(22) Filed: Jun. 2, 2014

(65) Prior Publication Data
US 2014/0358476 A1 Dec. 4, 2014

Related U.S. Application Data

(60) Provisional application No. 61/831,085, filed on Jun. 4, 2013.

(51) Int. Cl.
*G01B 11/24* (2006.01)
*G01N 21/47* (2006.01)
(Continued)

(52) U.S. Cl.
CPC ....... *G01N 21/4788* (2013.01); *G01M 11/025* (2013.01); *G01N 21/211* (2013.01);
(Continued)

(58) Field of Classification Search
CPC .......... G01B 11/24; G01B 2/21; G01B 11/30; G01N 21/211; G01N 21/4788;
(Continued)

(56) References Cited

U.S. PATENT DOCUMENTS 6,278,519 B1 8/2001 Rosencwaig et al.
6,608,690 B2 * 8/2003 Niu .................... G01B 11/0616
356/445

(Continued)

OTHER PUBLICATIONS

International Search Report and Written Opinion of the International Searching Authority dated Oct. 14, 2014, in International Patent Application No. PCT/US2014/040644, 17 pages.

*Primary Examiner* — Yoshihisa Ishizuka
(74) *Attorney, Agent, or Firm* — Womble Bond Dickinson (US) LLP

(57) ABSTRACT

Automatic determination of Fourier harmonic order for computation of spectral information for diffraction structures described. An embodiment of a method includes automatically determining a Fourier harmonic order for computation of spectral information for periodic structures, wherein the determination of the Fourier harmonic order is based at least in part on the pitches in each of multiple directions of the periodic structures, material properties of the periodic structures, and characteristics of the periodic structures in which the materials are contained; and computing the spectral information for the periodic structures based at least in part on the determined Fourier harmonic order.

29 Claims, 15 Drawing Sheets

(51) Int. Cl.
*G01N 21/956* (2006.01)
*G01M 11/02* (2006.01)
*G01N 21/21* (2006.01)
*G03F 7/20* (2006.01)
*G06F 17/40* (2006.01)
*G06F 19/00* (2018.01)
*G06F 11/30* (2006.01)
*H05K 13/08* (2006.01)
*G01B 11/30* (2006.01)

(52) U.S. Cl.
CPC ....... *G01N 21/956* (2013.01); *G03F 7/70625* (2013.01); *G01B 11/30* (2013.01); *G01B 2210/56* (2013.01); *G01N 2021/213* (2013.01); *G01N 2021/214* (2013.01); *G06F 11/30* (2013.01); *G06F 17/40* (2013.01); *G06F 19/00* (2013.01); *H05K 13/08* (2013.01)

(58) Field of Classification Search
CPC ........... G01N 21/956; G01N 2021/213; G01N 2021/214; G03F 7/70625; G01M 11/025; G06F 19/00; G06F 11/30; G06F 17/40; H05K 13/08
USPC ........................................................ 702/167
See application file for complete search history.

(56) References Cited

U.S. PATENT DOCUMENTS

| | | | |
|---|---|---|---|
| 6,734,967 B1 | 5/2004 | Piwonka-Corle et al. | |
| 6,839,145 B2* | 1/2005 | Niu | G01B 11/0616 356/445 |
| 6,943,900 B2* | 9/2005 | Niu | G01N 23/20 356/625 |
| 7,031,848 B2 | 4/2006 | Opsal et al. | |
| 7,277,189 B2* | 10/2007 | Niu | G03F 7/705 356/328 |
| 7,428,060 B2 | 9/2008 | Jin et al. | |
| 7,593,119 B2* | 9/2009 | Niu | G01N 23/20 356/625 |
| 7,831,528 B2 | 11/2010 | Doddi et al. | |
| 8,170,838 B2* | 5/2012 | Rabello | G06F 17/5018 359/237 |
| 8,645,109 B2* | 2/2014 | Dirks | G03F 7/705 703/2 |
| 2002/0035455 A1* | 3/2002 | Niu | G01N 23/20 703/4 |
| 2003/0103218 A1* | 6/2003 | Niu | G01B 11/0616 356/635 |
| 2003/0200063 A1* | 10/2003 | Niu | G01B 11/00 703/2 |
| 2003/0204325 A1* | 10/2003 | Niu | G01B 11/0616 702/27 |
| 2005/0256687 A1* | 11/2005 | Niu | G01N 23/20 703/6 |
| 2006/0066855 A1 | 3/2006 | Boef et al. | |
| 2006/0193532 A1 | 8/2006 | Roberts et al. | |
| 2007/0233404 A1 | 10/2007 | Lally et al. | |
| 2008/0049224 A1* | 2/2008 | Otsuki | G01N 21/211 356/370 |
| 2008/0249754 A1* | 10/2008 | Niu | G01N 23/20 703/6 |
| 2010/0157315 A1* | 6/2010 | Bischoff | G01B 11/24 356/612 |
| 2010/0165340 A1 | 7/2010 | Xu et al. | |
| 2010/0274521 A1* | 10/2010 | Rabello | G06F 17/5018 702/127 |
| 2011/0137625 A1* | 6/2011 | Dirks | G03F 7/705 703/2 |
| 2013/0158948 A1 | 6/2013 | Iloreta et al. | |

* cited by examiner

AUTOMATIC DETERMINATION OF FOURIER HARMONIC ORDER FOR COMPUTATION OF SPECTRAL INFORMATION FOR DIFFRACTION STRUCTURES

CROSS-REFERENCE TO RELATED APPLICATIONS

This application claims the benefit of U.S. Provisional Application No. 61/831,085, filed Jun. 4, 2013, the entire contents of which are hereby incorporated by reference herein.

TECHNICAL FIELD

Embodiments described herein generally relate to the field of optical metrology and, more particularly, automatic determination of Fourier harmonic order for computation of spectral information of diffraction structures.

BACKGROUND

A rigorous coupled wave analysis (RCWA) and similar algorithms have been widely used for the study and design of diffraction structures. In the RCWA approach, the profiles of periodic structures of a certain target structure are approximated by a given number of sufficiently thin planar grating slabs.

Specifically, RCWA involves three main operations, namely, the Fourier expansion of the field inside the grating, calculation of the eigenvalues and eigenvectors of a constant coefficient matrix that characterizes the diffracted signal, and solution of a linear system deduced from the boundary matching conditions. RCWA divides the problem into three distinct spatial regions: (1) the ambient region supporting the incident plane wave field and a summation over all reflected diffracted orders, (2) the grating structure and underlying non-patterned layers in which the wave field is treated as a superposition of modes associated with each diffracted order, and (3) the substrate containing the transmitted wave field.

In the establishment of RCWA and similar processes, a Fourier harmonic order is required for computation of spectral information for periodic structures of a larger target structure. However, the determination of an appropriate Fourier harmonic order for such computation can be difficult and require large computational costs.

SUMMARY

Embodiments are direct to automatic determination of Fourier harmonic order for computation of spectral information for diffraction structures.

In a first embodiment, a method includes automatically determining a Fourier harmonic order for computation of spectral information for periodic structures, wherein the determination of the Fourier harmonic order is based at least in part on the pitches in each of multiple directions of the periodic structures, material properties of the periodic structures, and characteristics of the periodic structures in which the materials are contained; and computing the spectral information for the periodic structures based at least in part on the determined Fourier harmonic order.

In a second embodiment, a machine-accessible storage medium has instructions stored thereon which cause a data processing system to perform a method automatic determination of Fourier harmonic order for computation of spectral information of diffraction structures, the method including automatically determining a Fourier harmonic order for computation of spectral information for periodic diffraction structures, wherein the determination of the Fourier harmonic order is based at least in part on the pitches in each of multiple directions of the periodic structures, material properties of the periodic structures, and characteristics of the periodic structures in which the materials are contained; and computing the spectral information for the periodic structures based at least in part on the determined Fourier harmonic order.

In a third embodiment, a system includes a processor, wherein the processor is to provide processing for automatically determining a Fourier harmonic order for computation of spectral information for diffraction structures, wherein the determination of the Fourier harmonic order for periodic structures of a target structure is based at least in part on the pitches in each of multiple directions of the periodic structures, material properties of the periodic structures, and characteristics of the periodic structures in which the materials are contained; and a memory for storage of data, the data including the determined Fourier harmonic order. The system is to generate spectral information for the periodic structures based at least in part on the determined Fourier harmonic order.

BRIEF DESCRIPTION OF THE DRAWINGS

Embodiments described here are illustrated by way of example, and not by way of limitation, in the figures of the accompanying drawings in which like reference numerals refer to similar elements.

DETAILED DESCRIPTION

Figure 1:
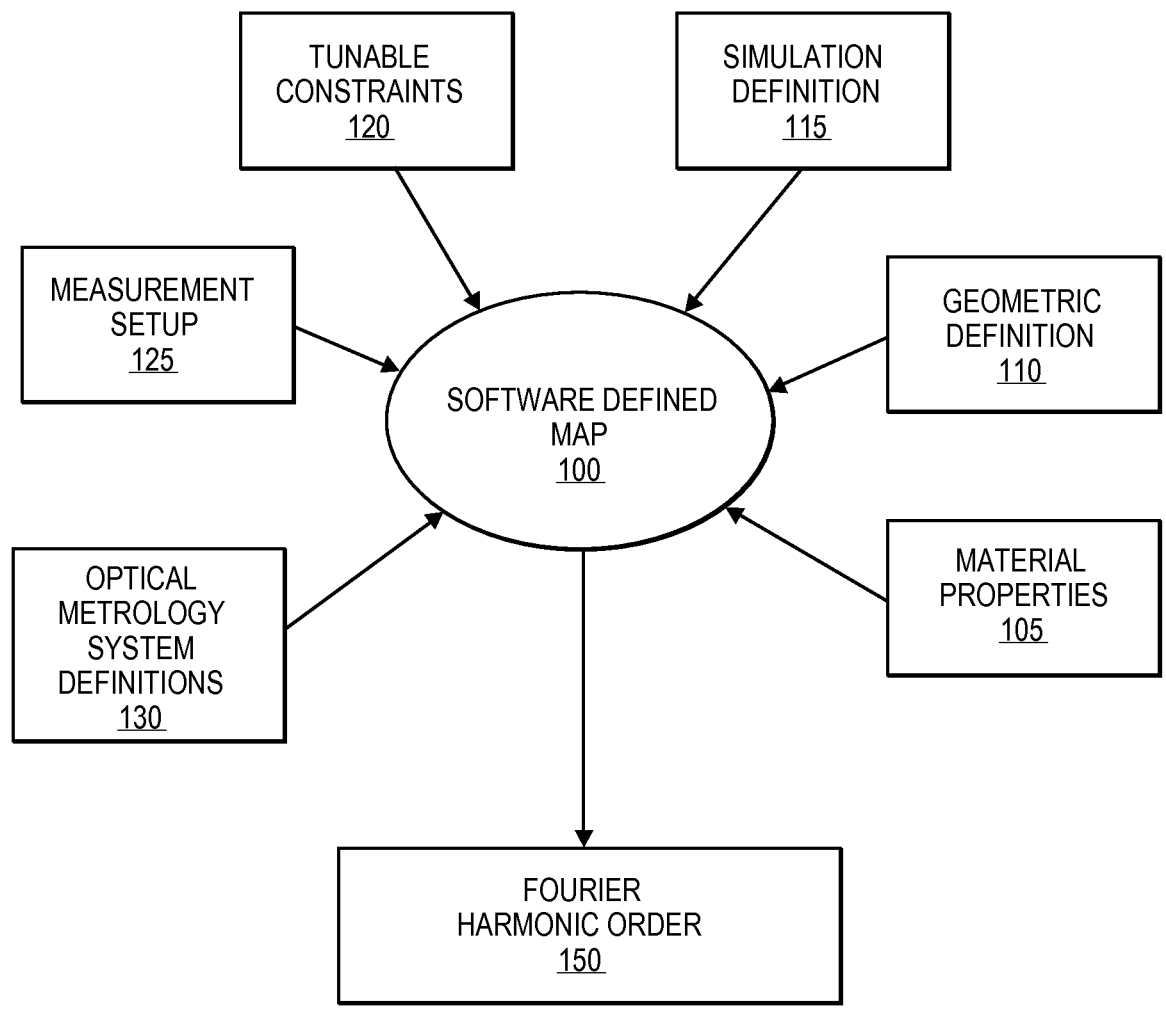
FIG. 1 is an illustration of inputs to an apparatus, system, or method to determine a Fourier harmonic order for computation of spectral information for periodic structures.

Embodiments described herein are generally directed to automatic determination of Fourier harmonic order for computation of spectral information for diffraction structures.

In the following description, numerous specific details are set forth, such as specific approaches to determination of Fourier harmonic order for computation of spectral information for periodic structures of a larger target structure, in order to provide a thorough understanding of embodiments of the present invention. It will be apparent to one skilled in the art that embodiments may be practiced without these specific details. In other instances, well-known processing operations, such as fabricating stacks of patterned material layers, are not described in detail in order to not unnecessarily obscure embodiments of the present invention. Furthermore, it is to be understood that the various embodiments shown in the figures are illustrative representations and are not necessarily drawn to scale.

In some embodiments, a method of evaluating periodic structures includes setting a Fourier harmonic order for computation of spectral information for the periodic structures independents of wavelength, or with wavelength changing according to a low-order polynomial function, a low-order polynomial function being a function with, for example, an order of no more than four.

As used herein, the term "periodic structures" (which may also be referred to as repeating structures) includes pseudo-periodic structures that are periodic over a finite area of a larger target structure, and that may be modeled as periodic structures. Further, periodic structures include repeating groups of multiple unit cells as well as a single repeating unit cell.

Certain conventional approaches exist for setting a Fourier harmonic order. For example: A first non-simulation approach may set the Fourier harmonic order based on the pitch of a structure, but without allowing different orders for X and Y directions. A second simulation approach may run RCWA with different Fourier harmonic orders and test the convergence of each. A modified simulation approach may attempt to predict the convergence of RCWA from the size and material properties of all discretized regions.

However, the conventional approaches suffer from significant deficiencies in operation. With regard to the first method, basing a Fourier harmonic order on pitch can be too limiting, being unsuitable for geometries with a high pitch ratio between X and Y directions, and does not take into account other aspects of the diffraction structure, such as material properties or geometric complexity of a structure.

With regard to the second approach, providing multiple simulations can be impractically slow, particularly if attempting to make the Fourier harmonic order wavelength independent. Further, simulation convergence can be a poor predictor of what order is needed for simulation reliability, and may vary considerably across the parameter space. Simulation based results also tend to be erratic, producing undesirably extreme order settings. The modified method, while operating faster than the second method, suffers from similar limitations.

In some embodiments, a process for determination of harmonic order may be run locally on a workstation, rather than requiring extensive computational resources. In some embodiments, a process for determination of harmonic order does not require electromagnetic simulation, and thus runs very quickly in comparison with conventional processes utilizing simulation. In some embodiments, an operation to determine a Fourier harmonic order is efficient and produces consistently reasonable results. Subsequent computationally intensive electromagnetic solver calculation, such as RCWA calculations, may then be conducted efficiently and accurately utilizing a reasonably selected harmonic order.

In some embodiments, an apparatus, system, or method provides an efficient process for setting the Fourier harmonic order for computation of spectral information for periodic structures in optical metrology. In some embodiments, the apparatus, system, or method is applicable for optical CD (critical dimension) measurement using any one or combination of spectroscopic, single wavelength, or angle resolved ellipsometry or reflectometry techniques.

In some embodiments, an apparatus, system, or method considers multiple factors to efficiently reach an appropriate order setting. In some embodiments, the apparatus, system, or method considers in combination: (a) the pitches in each direction of periodic structures (relative dimensions of a unit cell of the periodic structures), (b) material properties of the periodic structures, and (c) characteristics of the periodic structures in which the materials are contained. In some embodiments, the consideration includes interrelationships between any of the pitches, material properties, and characteristics of the periodic structures. In some embodiments, characteristics include one or both of qualitative and quantitative characteristics. In some embodiments, the characteristics may include, for example, whether a layer in which a particular material is contained is a film, or varies in one or two dimensions.

In some embodiments, wavelength dependence of a resulting harmonic order is further constrained to a low order polynomial function. In some embodiments, adjustable settings allow refinement of the way the inputs are used and how the output is constrained. In some embodiments, other measurement system definitions, measurement setup specifics, and adjustments for alternative simulators may also be included.

FIG. 1 is an illustration of inputs to an apparatus, system, or method to determine a Fourier harmonic order for computation of spectral information for periodic structures. In some embodiments, the periodic structures may include microelectronic structures on a substrate. The periodic structures (repeating structures) may be unit cells or groups of unit cells within a larger target structure. As illustrated, a software defined map 100 or other similar implementation is to produce a Fourier harmonic order 150 based on inputs to the map 100.

In Some Embodiments, the Inputs to the Software Defined Map 100 May Include:

Material properties, including permittivity, of the materials making up the periodic structures 105; and geometric definition of the periodic structures 110. In some embodiments, such elements includes the pitches in each direction of a structure, the repeating nature of one more structures, and the characteristics of the periodic structure within which the materials are contained.

In Some Embodiments, the Inputs to the Software Defined Map 100 Further Include:

A simulation definition 115;

Tunable constraints 120, where such constraints may be predefined by a user;

Measurement setup 125, including a specific setup of optical metrology elements, including the manner in which a structure is coupled with the optical metrology system; and Optical Metrology System Definitions 130.

Figure 2:
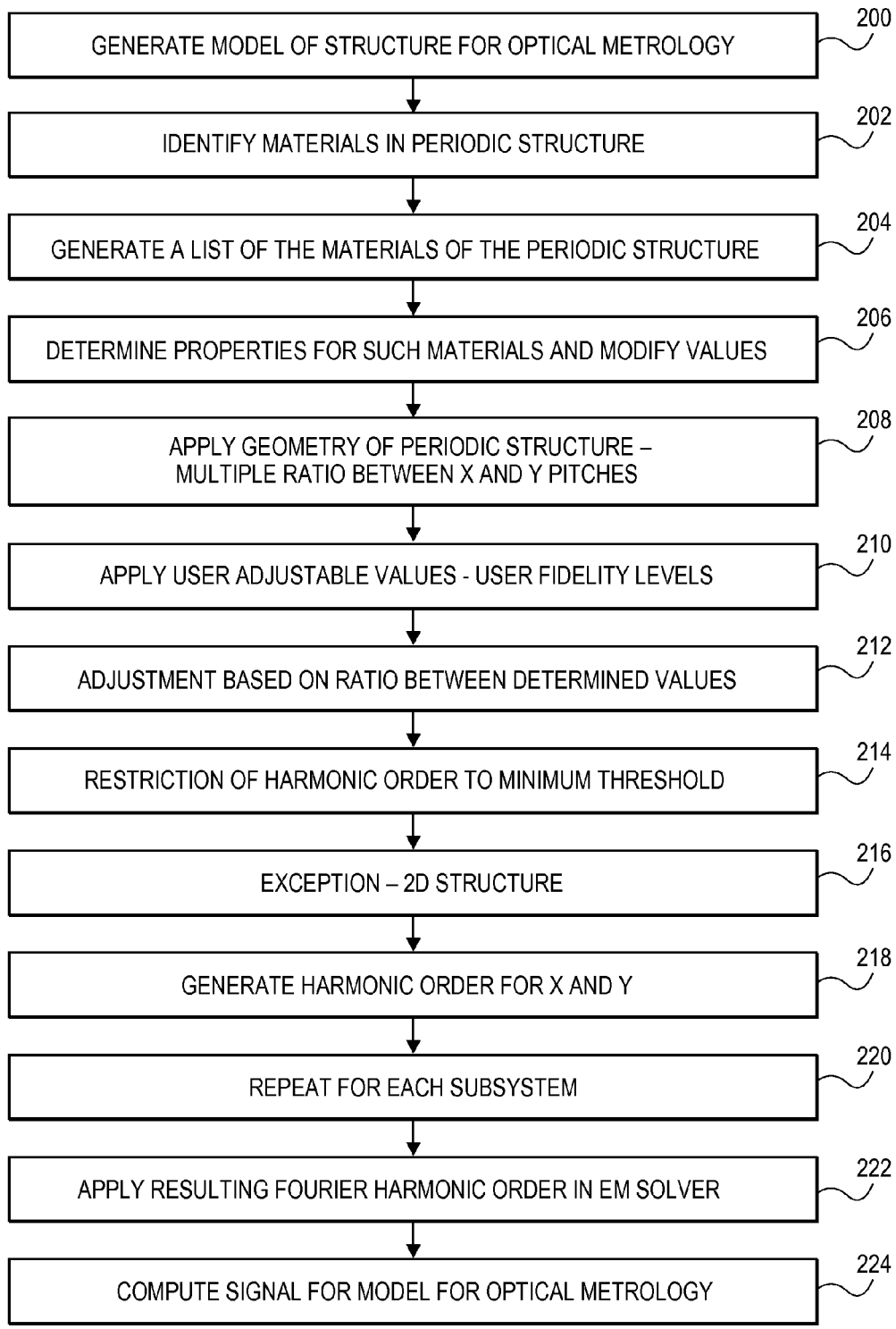
FIG. 2 illustrates an embodiment of a process for determination of a Fourier harmonic order for computation of spectral information for periodic structures.

FIG. 2 illustrates an embodiment of a process for determination of a Fourier harmonic order for computation of spectral information for periodic structures. In some embodiments, an apparatus, system, or method provides a particular implementation in which a Fourier harmonic order is determined based upon the pitches in each of multiple direction of a structure, the material properties of the structure, and characteristics of the structures in which the materials are contained. In some embodiments, the determination is based at least in part on interrelationships between any of such elements. While FIGS. 2 and 3A-3C provide examples of particular implementations for the determination of Fourier harmonic orders for periodic structures, embodiments are not limited to these implementations, and may include varying details in the generation of the harmonic order and varying order of the elements in the process flow.

In some embodiments, in the modeling of structures for optical metrology 200, a process for determination of a Fourier harmonic order for computation of spectral information for periodic structures includes automatically:

(a) Identifying the materials in a period structure 202, such as by traversing each layer of the structures;

(b) Generating a list of the materials of a periodic structure, where the list may include materials as found in both X- and Y-directions in the periodic structure 204.

(c) Determining properties of the materials 206. In some embodiments, the properties may include determining $\epsilon$ (epsilon, referring to the permittivity of a material, permittivity being the ability of a material to resist the formation of an electric field) values for each simulation wavelength for each such material, and modifying such $\epsilon$ values including user configurable values.

(d) Applying values based on geometry of the periodic structure 208, which may include applying a ratio between the X and Y pitches of a periodic structure.

(e) Applying user adjustable values 210, which may include application of user adjustable fidelity levels. In some embodiments, a fidelity level may be transformed, such as with a logarithmic value, and may be scaled to constrain values.

(f) Adjustment of harmonic order based on ratio between determined values 212, such as multiplying minimum TO levels by ratio between values reduced by modified fidelity level and value multiplied by modified $\epsilon$ value.

(g) Restriction of harmonic order to be a minimum threshold 214.

(h) In an exception, if the periodic structure is entirely two-dimensional (2D), maximum and minimum values may be set to zero for the corresponding X or Y direction 216.

(i) Generating a wavelength dependent harmonic order based on the calculated results, such as, in one example, by generating a line between minimum and maximum values 218. However, embodiments are not limited to this implementation.

(j) Repeating processes for each subsystem of the periodic structures 220. In some embodiments, the resulting Fourier harmonic order values are applied in in electromagnetic solver, such as RCWA 222 and a signal for the model is generated for the optical metrology process 224.

Figure 3A:
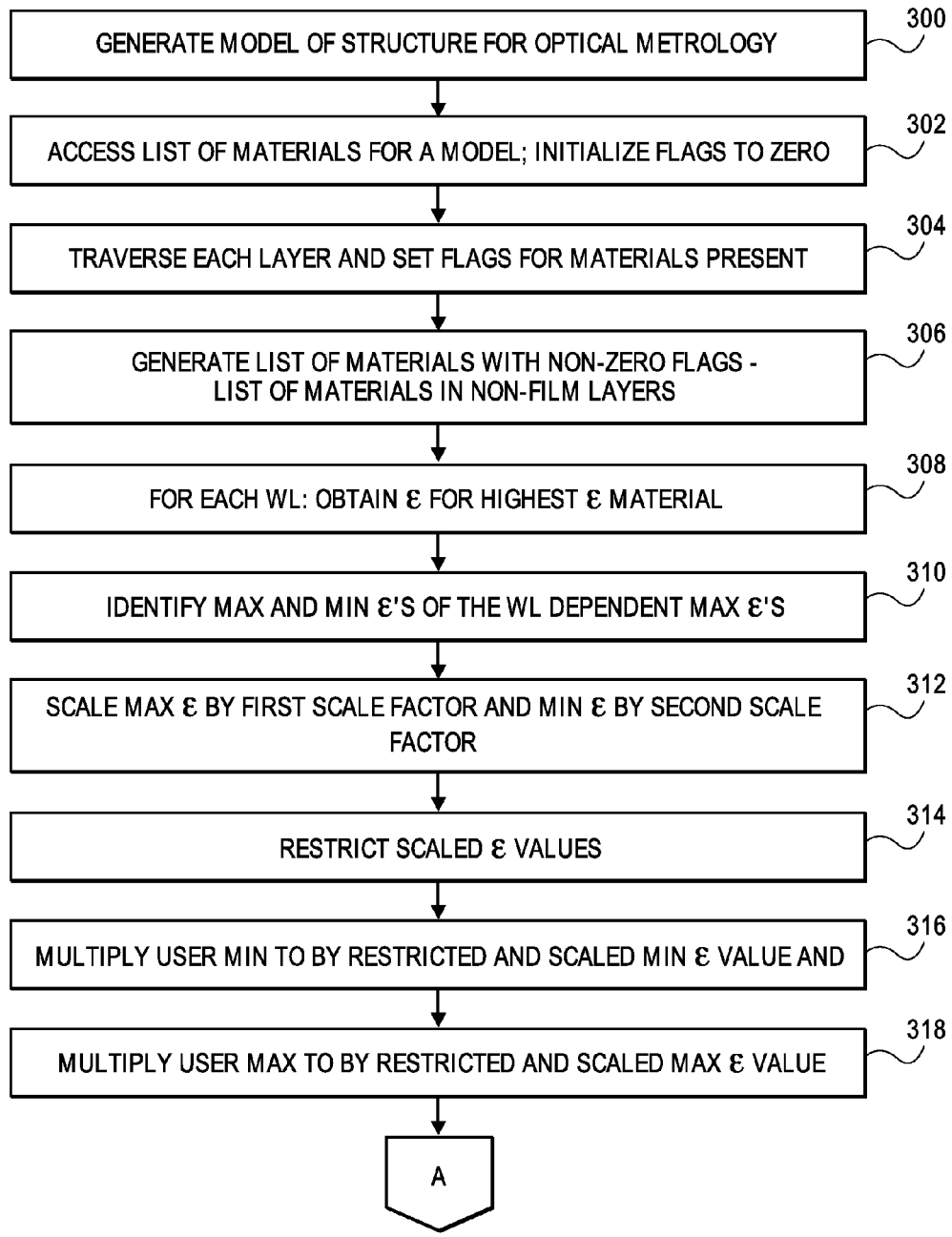
FIGS. 3A, 3B, and 3C illustrate details of an embodiment of a process for determination of a Fourier harmonic order for computation of spectral information for periodic structures.
Figure 3B:
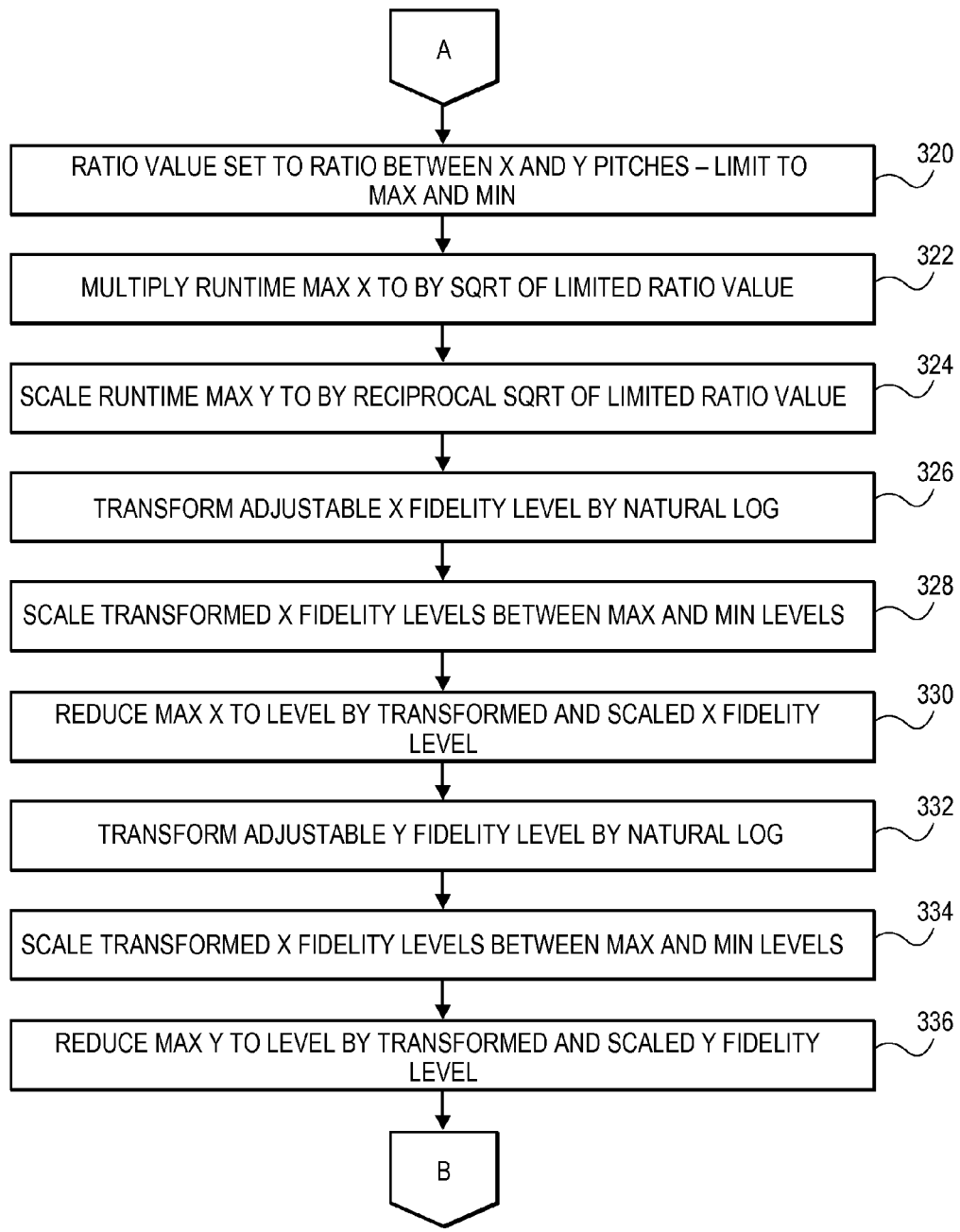
Figure 3C:
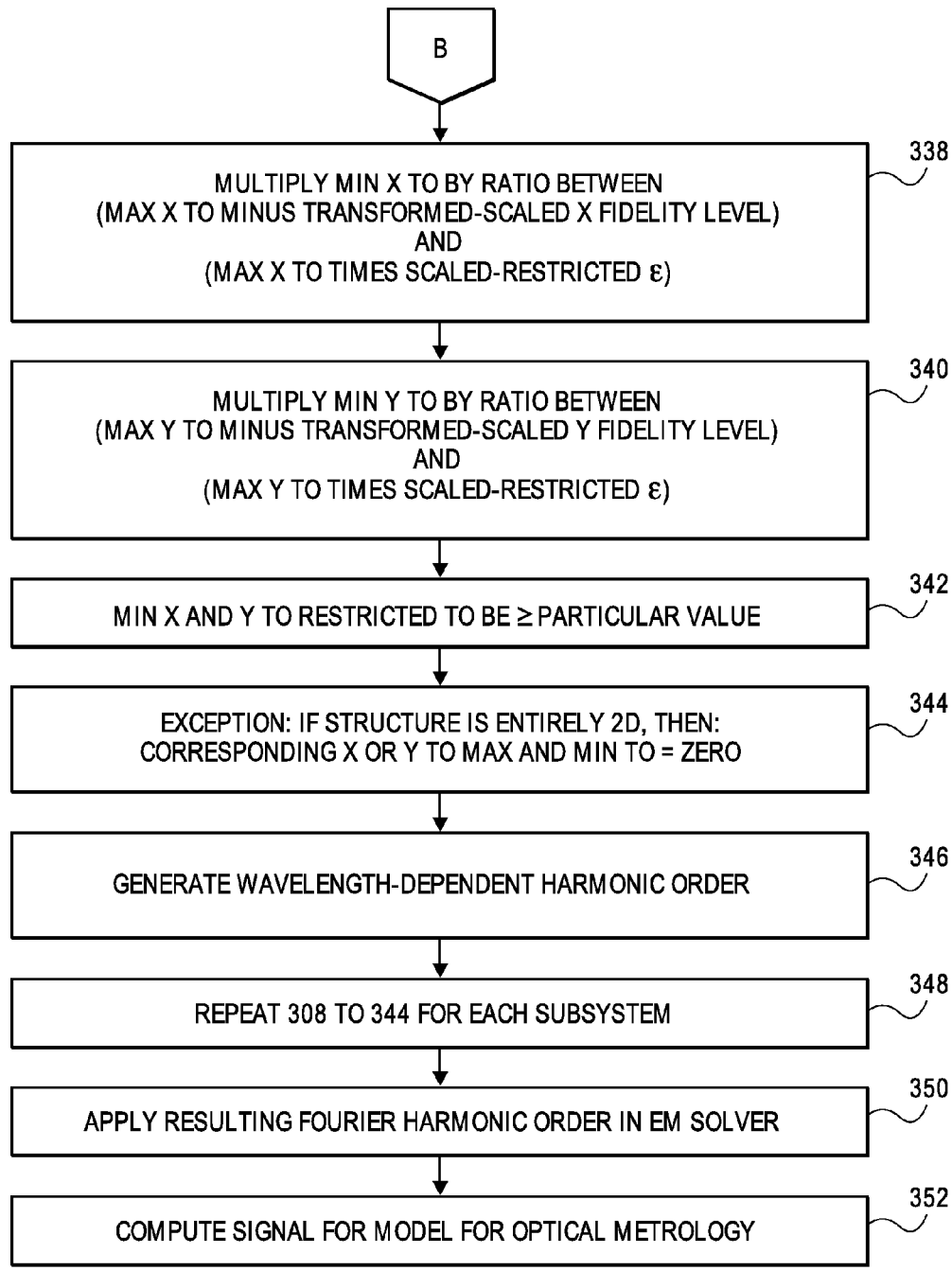

FIGS. 3A, 3B, and 3C illustrate details of an embodiment of a process for determination of a Fourier harmonic order for computation of spectral information for periodic structures. In some embodiments, the process illustrated in FIG. 2 may include some or all of the details illustrated in FIGS. 3A, 3B, and 3C.

As illustrated in FIG. 3A, in the modeling of structures for optical metrology 300, a process for determination of a Fourier harmonic order for computation of spectral information for periodic structures includes:

(a) In some embodiments, a list of materials contain every, or substantially every, material that will be present in a model of a structure, and the process includes accessing such list of materials 302. In some embodiments, for every material in the list, each flag of a pair of flags is initialized to zero.

In some embodiments, the layers of the model are traversed and flags are set for materials that are present 304. For example, if a layer contains multiple materials in the X direction, a first flag of a pair of flags is set for each material in that layer. If the layer contains multiple materials in the Y-direction, a second flag of a pair of flags is set for each of such materials.

(b) In some embodiments, a list of materials with nonzero flags is constructed 306, the list being a combined list for both X and Y directions. Stated in another way, the result is a list of materials that exist in non-film layers.

(c) In some embodiments, for each simulation wavelength, the $\epsilon$ (epsilon, referring to the permittivity of a material, permittivity being the ability of a material to resist the formation of an electric field) for the highest $\epsilon$ material is obtained 308.

In some embodiments, the maximum and minimum of the set of wavelength dependent maximum $\epsilon$'s are then identified 310, and the maximum and minimum $\epsilon$'s are then scaled by a first scale factor and a second scale factor respectively 312. In an example, the maximum is then scaled by a first scale factor of five, and the minimum is scaled by a second scale factor of two. In some embodiments, the scaled values are also restricted to be no greater than one 314.

In some embodiments, a user configurable minimum Fourier harmonic order (TO, for Truncation Order) is then multiplied by the scaled and restricted minimum epsilon 316, and a user configurable maximum TO is scaled by the scaled and restricted maximum $\epsilon$ 318.

Continuing the Process as Illustrated in FIG. 3B:

(d) In some embodiments, a ratio value is set to the ratio between the X and Y pitch, with the value being limited to certain maximum and minimum values (and being referred to herein as a limited ratio value) 320. In an example, the value is limited to be no larger than two (2.0) or less than one-half (0.5).

In some embodiments, a run-time configurable maximum X TO (X-direction Truncation Order) is then multiplied by the square root of the limited ratio value 322. In some embodiments, a run-time configurable maximum Y TO (Y-direction Truncation Order) is scaled by the reciprocal square root of the limited ratio value 324.

(e) In some embodiments, a user adjustable X fidelity level is limited to be between a minimum value and a maximum value, where such values may be 1 and 15 respectively. In some embodiments, the X fidelity level is then transformed with a natural logarithm 326. In some embodiments, the transformed X fidelity level is then scaled to be between a lower value and an upper values, the lower and upper values being, for example, zero (0) and the difference between the maximum and minimum X TO levels 328. In some embodiments, the maximum X TO level is then decreased by that transformed and scaled fidelity level 330. In this process, the scaling prevents the maximum from decreasing to below the existing minimum. In some embodiments, a user adjustable Y fidelity level is similarly limited to be between a minimum value and a maximum value 332 and transformed with a natural logarithm 334, with the maximum Y TO level is similarly decreased by the transformed and scaled user adjustable Y fidelity level 336.

Continuing the Process as Illustrated in FIG. 3C:

(f) In some embodiments, the minimum X TO level is multiplied by the ratio between the maximum X TO reduced by the transformed and scaled X fidelity level (from 330) and the maximum X TO multiplied by the scaled and restricted $\epsilon$ value (from 318) 338. In some embodiments, the minimum Y TO level is multiplied by the ratio between the maximum X TO reduced by the transformed and scaled X fidelity level (from 330) and the maximum X TO multiplied by the scaled and restricted $\epsilon$ value (from 318) 340. In some embodiments, these operations adjust the minimum X and Y TO levels by pitch and desired fidelity level.

(g) In some embodiments, the minimum X TO level and Y TO level are restricted to be no less than a particular value 342. For example, the minimum X TO level and minimum Y TO level are restricted to be no less than two ($\geq 2$).

(h) In an exception, in some embodiments, if the periodic structure is entirely two-dimensional (2D), based on an accumulation for the flags (as set in 304), the corresponding X or Y TO maximums and minimums are set to zero 344.

(i) In some embodiments, a wavelength dependent harmonic order for X and Y is generated based on the calculated results, such as, in one example, generating a line between the maximum and minimum X TO values, with the maximum at the shortest wavelength 346.

(j) In some embodiments, the process of (c) through (h) (308 through 344) is repeated for each subsystem 348. In some embodiments, the resulting Fourier harmonic order values are applied in RCWA 350, and a model of a structure is generated for the optical metrology process 352.

Figure 4:
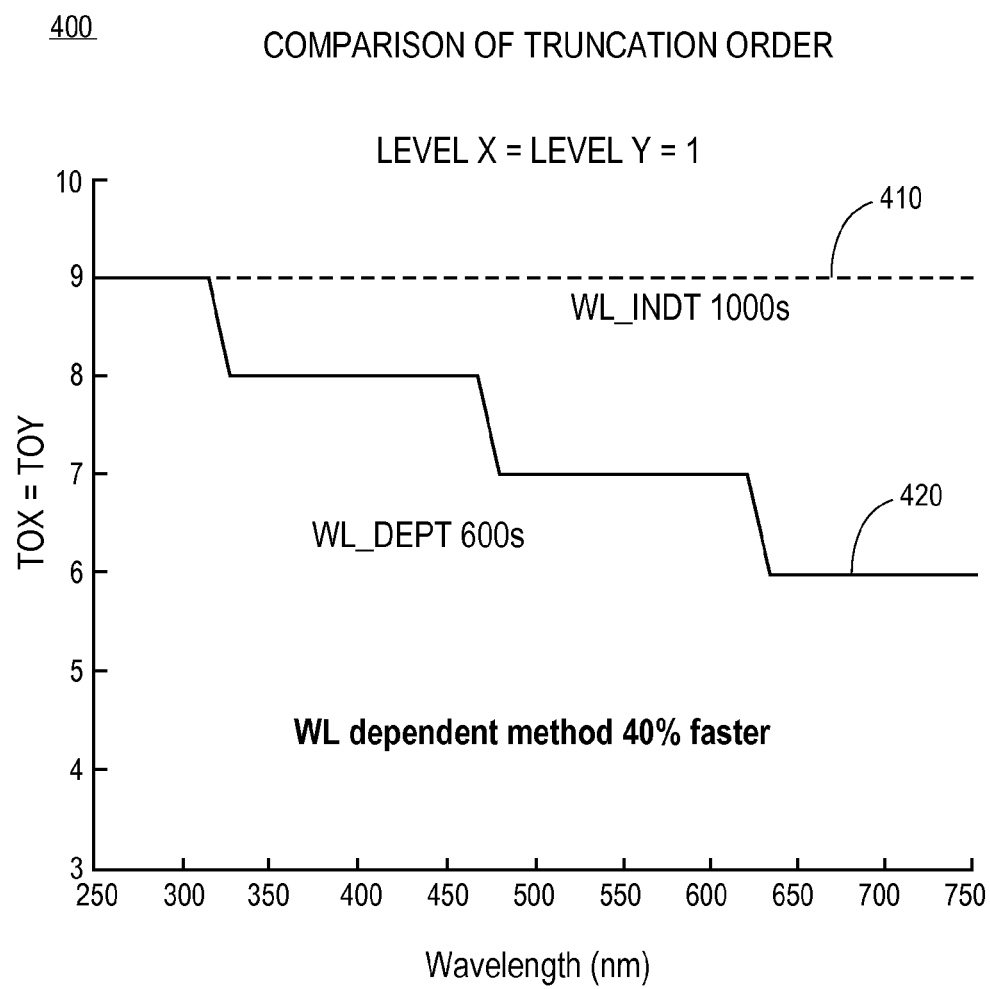
FIG. 4 illustrates a first example of Fourier harmonic order as determined according to an embodiment.
Figure 5:
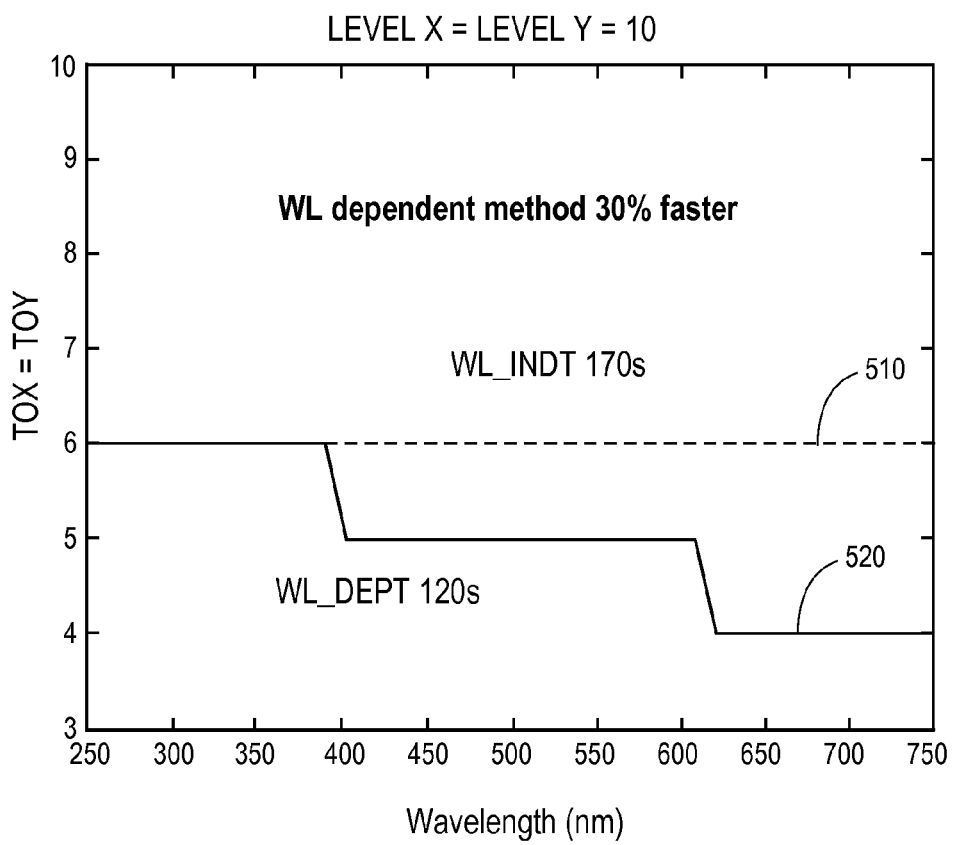
FIG. 5 illustrates a second example of Fourier harmonic order as determined according to an embodiment.

FIG. 4 illustrates a first example of Fourier harmonic order as determined according to an embodiment. As illustrated in the comparison of truncation order 400 in FIG. 4, the harmonic order may be constrained to be independent of wavelength 410, or to change linearly with wavelength 420. As shown in FIG. 4, the wavelength dependent harmonic order 420 is calculated 40 percent faster than the wavelength independent harmonic order 410 (600 seconds versus 1000 seconds) with similar quality. FIG. 5 illustrates a second example of Fourier harmonic order as determined according to an embodiment, wherein the harmonic order may be constrained to be independent of wavelength 510, or to change linearly with wavelength 520. As shown in the comparison of truncation order 500 in FIG. 5, the wavelength dependent harmonic order 520 is calculated 30 percent faster than the wavelength independent harmonic order 510 (120 seconds versus 170 seconds) with similar quality.

In some embodiments, results of the determination process are independent of the choice of nominal geometric values, and don't vary erratically by wavelength. Further, the harmonic order determination is extremely fast, and the RCWA process may be conducted more efficiently and reliably than if the Fourier harmonic order is set manually by the user.

In some embodiments, functions can be used to constrain the wavelength dependence, including generating a harmonic order that is independent of wavelength, or that varies linearly with length. Other sufficiently qualitative geometric heuristics can be added. More specifically:

(a) It may be unnecessary to flag a material in the X or Y direction based on any part of that layer containing multiple materials in that direction. In some embodiments, if the material itself uniformly spans a section of that layer without boundaries in the direction under consideration, then the corresponding X or Y flag does not need to be set. Other refinements based on geometric dimensions are also possible, provided that they apply acceptably well across the whole parameter space.

(b) In some embodiments, separate lists of materials may be maintained for which X and Y flags are set. In other words, there will be a first list of materials in 3D or X 2D layers, and a second list for materials that are in 3D or Y 2D layers. In some embodiments, the process may be performed independently on the two different lists, to determine material-based TO constraints that are independent for X and Y.

(c) In some embodiments, it may be desirable to keep track of which wavelengths the maximum $\epsilon$'s occur at, for a better or more conservative fit. It may be desirable to keep track of additional wavelength dependent maximum epsilons if a higher order wavelength dependent TO constraint is to be used. For instance, if the wavelength dependent TO were to be constrained to a quadratic function, the maximums at the longest and shortest wavelengths could be used, along with the largest maximum for the intervening wavelengths and what wavelength it occurs at.

(d) In some embodiments, other comparable processes may be utilized to ensure that TO settings are not impractically high or low. Azimuth angle is an example of a measurement system definition or setting that could be useful to take into account in determining harmonic order. In some embodiments, adjustments may also be made according to the speed and requirements of the RCWA solver used, if alternative formulations are used in suitable situations.

(e) In some embodiments, other processes may be utilized to provide the user with some control over the desired fidelity of the EM (electromagnetic) simulation. For instance, the choice of a logarithmic scheme is not required, and is implemented for conceptual and user interface compatibility with possible methods that would use EM simulation and noise considerations. In some embodiments, alternative schemes may be combined with (c) (elements 308-318 of FIG. 3A) because these each impose configurable limitations on TO.

(f) The exact manner in which pitch is taken into account depends on the constraining methods selected for (d) (elements 320-324 of FIG. 3B) and (e) (elements 326-336 of FIG. 3B), and depends on whether reserving a pitch dependent X and Y TO ratio is considered more or less important than satisfying strict maximum and minimum constraints. In some embodiments, geometry and materials may also be taken into account in a more detailed way when deciding on the impact of pitch.

(g) In some embodiments, forcing the TO to be at least 2 may or may not be necessary and desirable depending on what is done in (d), (e), and (f), and depending on how conservative of a TO setting is desired.

(h). The determination of whether the diffraction structure is 2D in the X or Y direction can be accomplished in a variety of equivalent ways. For example, if separate X and Y material lists are maintained in (b) (element 306 of FIG. 3A), then there will be no materials in one or the other list for a 2D structure, in which case X and Y TO constraints could be set to zero in (c).

(i) The example of a constraint of the wavelength dependent TO to a line (such as the examples described for element 218 of FIG. 2 and element 346 of FIG. 3C) is made for conceptual and user interface simplicity. In some embodiments, a simpler alternative is to constrain the TO to a constant. In some embodiments, a parabola or some other function may be implemented, with appropriate adjustments in the calculation of the harmonic order.

(j) In some embodiments, the process of applying heuristics and model based constraints may be reordered or adjusted to produce slightly different results, or to eliminate redundant steps depending on the software architecture.

In Some Embodiments:

An apparatus, system, or process provides for determination of Fourier harmonic order with automatic dependence on pitch.

An apparatus, system, or process for determination of Fourier harmonic order utilizes wavelength dependent material properties in conjunction with geometric characteristics that don't depend on nominal values.

An apparatus, system, or process provides for determination of Fourier harmonic order with a result that is constrained to a simple function of wavelength.

This application incorporates by reference in its entirety for all purposes, the U.S. patent application Ser. No. 13/712,734 filed Dec. 12, 2012, now U.S. Pat. No. 9,127,927, and titled "Techniques for Optimized Scatterometry."

In general, orders of a diffraction signal may be simulated as being derived from a periodic structure. The zeroth order represents a diffracted signal at an angle equal to the angle of incidence of a hypothetical incident beam, with respect to the normal N of the periodic structure. Higher diffraction orders are designated as +1, +2, +3, −1, −2, −3, etc. Other orders known as evanescent orders may also be considered. In accordance with an embodiment, a simulated diffraction signal is generated for use in optical metrology. For example, profile parameters, such as structural shape and film thicknesses, may be modeled for use in optical metrology. Optical properties of materials, such as index of refraction and coefficient of extinction, (n & k), in structures may also be modeled for use in optical metrology.

Figure 6:
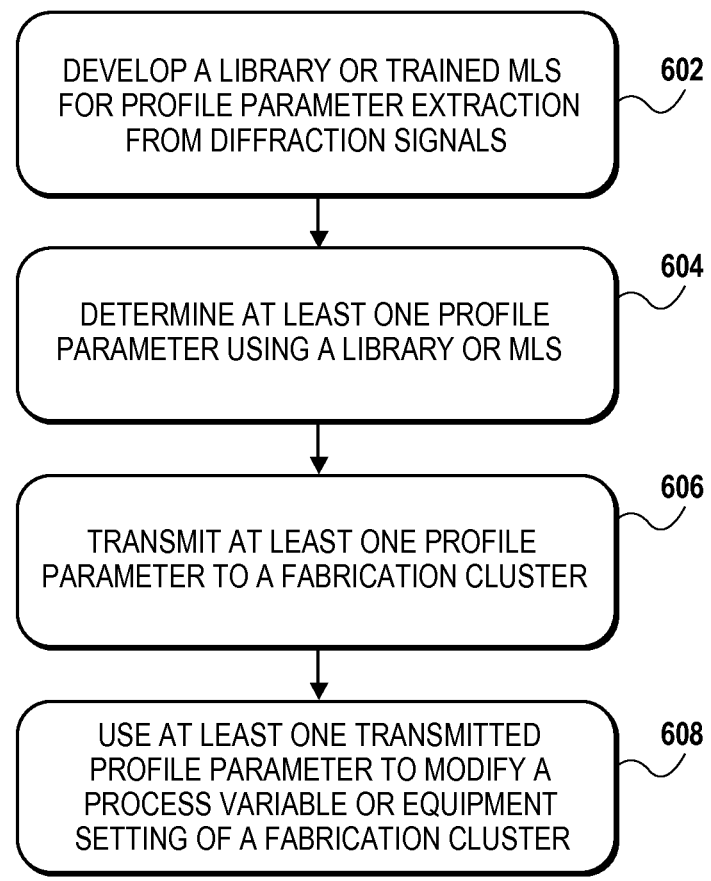
FIG. 6 depicts a flowchart representing an exemplary series of operations for determining and utilizing structural parameters for automated process and equipment control in accordance with an embodiment.

Calculations based on simulated diffraction orders may be indicative of profile parameters for a patterned film, such as a patterned semiconductor film or structure based on a stack of films, and may be used for calibrating automated processes or equipment control. FIG. 6 depicts a flowchart 600 representing an exemplary series of operations for determining and utilizing structural parameters for automated process and equipment control in accordance with an embodiment.

Referring to operation 602 of flowchart 600, a library or trained machine learning systems (MLS) is developed to extract parameters from a set of measured diffraction signals. In operation 604, at least one parameter of a structure is determined using the library or the trained MLS. In operation 606, the at least one parameter is transmitted to a fabrication cluster configured to perform a processing operation, where the processing operation may be executed in the semiconductor manufacturing process flow either before or after measurement operation 604 is made. In operation 608, the at least one transmitted parameter is used to modify a process variable or equipment setting for the processing operation performed by the fabrication cluster.

For a more detailed description of machine learning systems and algorithms, see U.S. Pat. No. 7,831,528, entitled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety. For a description of diffraction order optimization for two-dimensional repeating structures, see U.S. Pat. No. 7,428,060, entitled OPTIMIZATION OF DIFFRACTION ORDER SELECTION FOR TWO-DIMENSIONAL STRUCTURES, filed on Mar. 24, 2006, which is incorporated herein by reference in its entirety.

Figure 7:
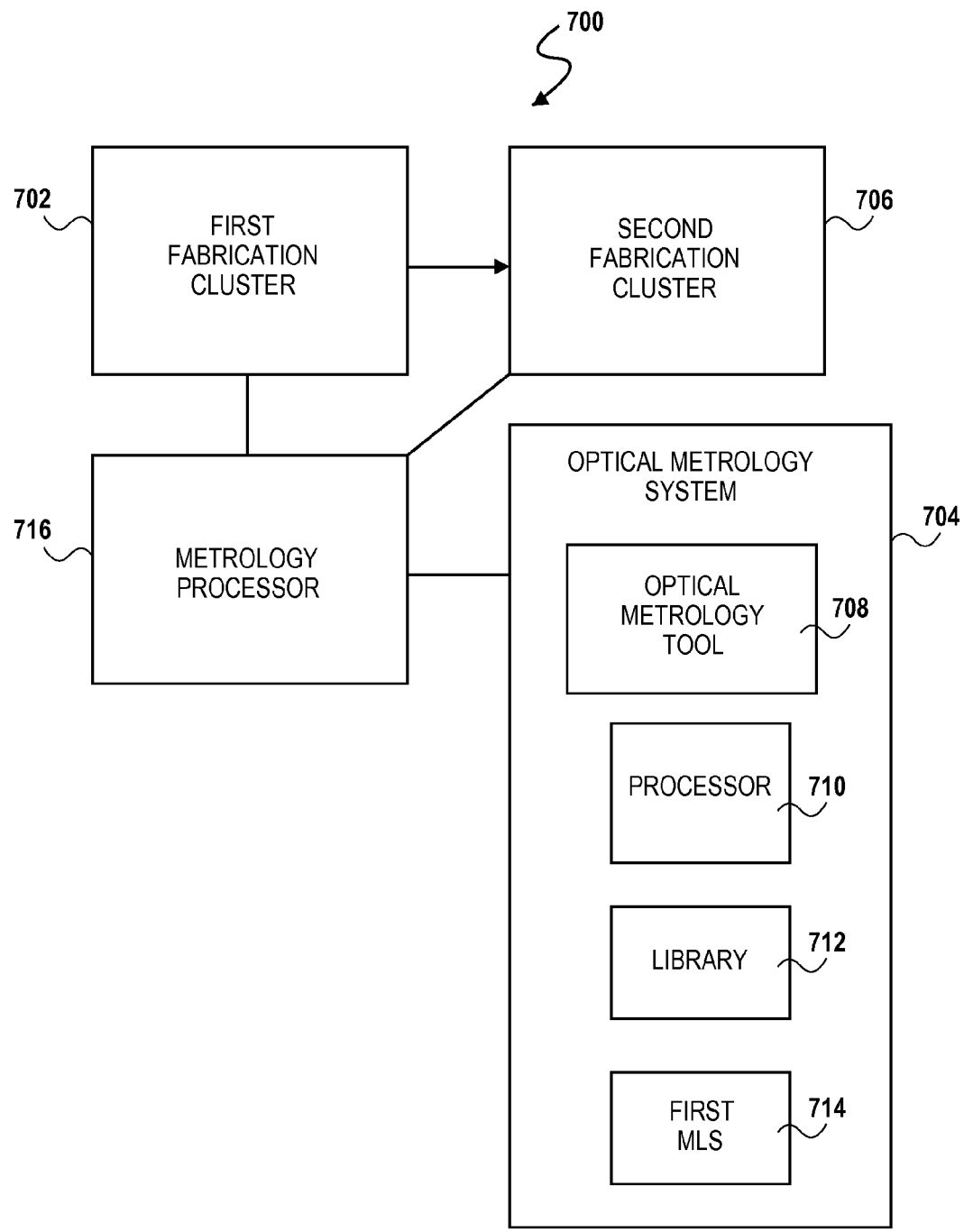
FIG. 7 is an exemplary block diagram of a system for determining and utilizing structural parameters for automated process and equipment control in accordance with an embodiment.

FIG. 7 is an exemplary block diagram of a system 700 for determining and utilizing structural parameters, such as profile or film thickness parameters, for automated process and equipment control in accordance with an embodiment. System 700 includes a first fabrication cluster 702 and optical metrology system 704. System 700 also includes a second fabrication cluster 706. Although the second fabrication cluster 706 is depicted in FIG. 7 as being subsequent to first fabrication cluster 702, it should be recognized that second fabrication cluster 706 can be located prior to first fabrication cluster 702 in system 700 (and, e.g., in the manufacturing process flow).

In one exemplary embodiment, optical metrology system 704 includes an optical metrology tool 708 and processor 710. Optical metrology tool 708 is configured to measure a diffraction signal obtained from the structure. If the measured diffraction signal and the simulated diffraction signal match, one or more values of the profile or film thickness parameters are determined to be the one or more values of the profile or film thickness parameters associated with the simulated diffraction signal.

In one exemplary embodiment, optical metrology system 704 can also include a library 712 with a plurality of simulated diffraction signals and a plurality of values of, e.g., one or more profile or film thickness parameters associated with the plurality of simulated diffraction signals. As described above, the library can be generated in advance. Processor 710 can be used to compare a measured diffraction signal obtained from a structure to the plurality of simulated diffraction signals in the library. When a matching simulated diffraction signal is found, the one or more values of the profile or film thickness parameters associated with the matching simulated diffraction signal in the library is assumed to be the one or more values of the profile or film thickness parameters used in the wafer application to fabricate the structure. In some embodiments, the processor 710 provides some or all of the processing for automatic determination of Fourier harmonic order for computation of spectral information for diffraction structures.

System 700 also includes a metrology processor 716. In one exemplary embodiment, processor 710 can transmit the one or more values of the, e.g., one or more profile or film thickness parameters to metrology processor 716. Metrology processor 716 can then adjust one or more process parameters or equipment settings of first fabrication cluster 702 based on the one or more values of the one or more profile or film thickness parameters determined using optical metrology system 704. Metrology processor 716 can also adjust one or more process parameters or equipment settings of the second fabrication cluster 706 based on the one or more values of the one or more profile or film thickness parameters determined using optical metrology system 704. As noted above, fabrication cluster 706 can process the wafer before or after fabrication cluster 702. In another exemplary embodiment, processor 710 is configured to train machine-learning system 714 using the set of measured diffraction signals as inputs to machine learning system 714 and profile or film thickness parameters as the expected outputs of machine learning system 714.

Figure 8A:
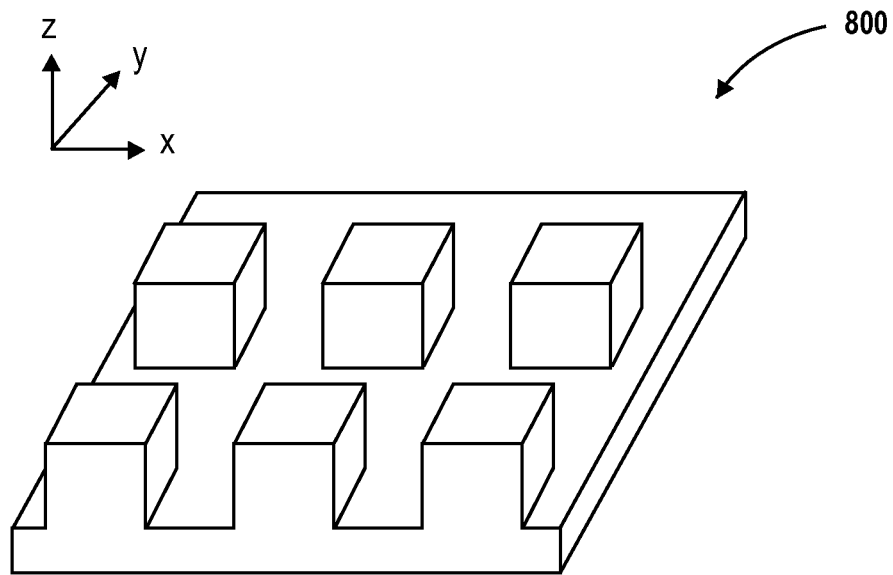
FIG. 8A depicts a periodic grating having a profile that varies in the x-y plane for modeling in accordance with an embodiment.

In an embodiment, optimizing a model of a structure includes using a three-dimensional grating structure. The term "three-dimensional grating structure" is used herein to refer to a structure having an x-y profile that varies in two horizontal dimensions in addition to a depth in the z-direction. For example, FIG. 8A depicts a periodic grating 800 having a profile that varies in the x-y plane for modeling in accordance with an embodiment. The profile of the periodic grating varies in the z-direction as a function of the x-y profile.

Figure 8B:
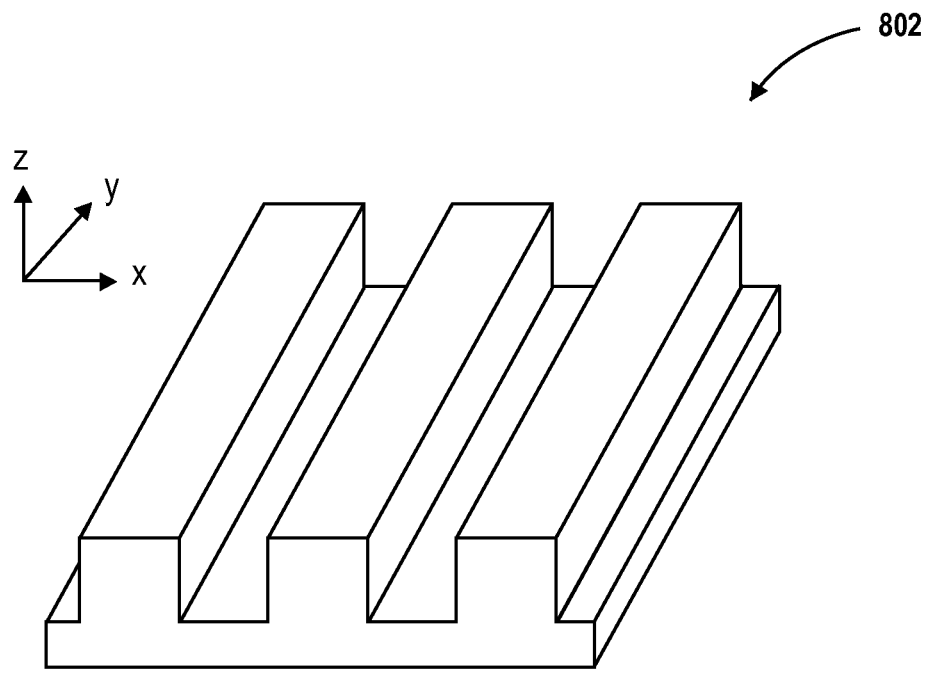
FIG. 8B depicts a periodic grating having a profile that varies in the x-direction but not in the y-direction for modeling in accordance with an embodiment.

In an embodiment, optimizing a model of a structure includes using a two-dimensional grating structure. The term "two-dimensional grating structure" is used herein to refer to a structure having an x-y profile that varies in only one horizontal dimension in addition to a depth in the z-direction. For example, FIG. 8B depicts a periodic grating 802 having a profile that varies in the x-direction but not in the y-direction for modeling in accordance with an embodiment. The profile of the periodic grating varies in the z-direction as a function of the x profile. It is to be understood that the lack of variation in the y-direction for a two-dimensional structure need not be infinite, but any breaks in the pattern are considered long range, e.g., any breaks in the pattern in the y-direction are spaced substantially further apart than the breaks in the pattern in the x-direction.

Embodiments may be suitable for a variety of film stacks. For example, in an embodiment, a method for optimizing a parameter of a critical dimension (CD) profile or structure is performed for a film stack including an insulating film, a semiconductor film and a metal film formed on a substrate. In an embodiment, the film stack includes a single layer or multiple layers. Also, in an embodiment, an analyzed or measured grating structure includes both a three-dimensional component and a two-dimensional component. For example, the efficiency of a computation based on simulated diffraction data may be optimized by taking advantage of the simpler contribution by the two-dimensional component to the overall structure and the diffraction data thereof.

Figure 9:
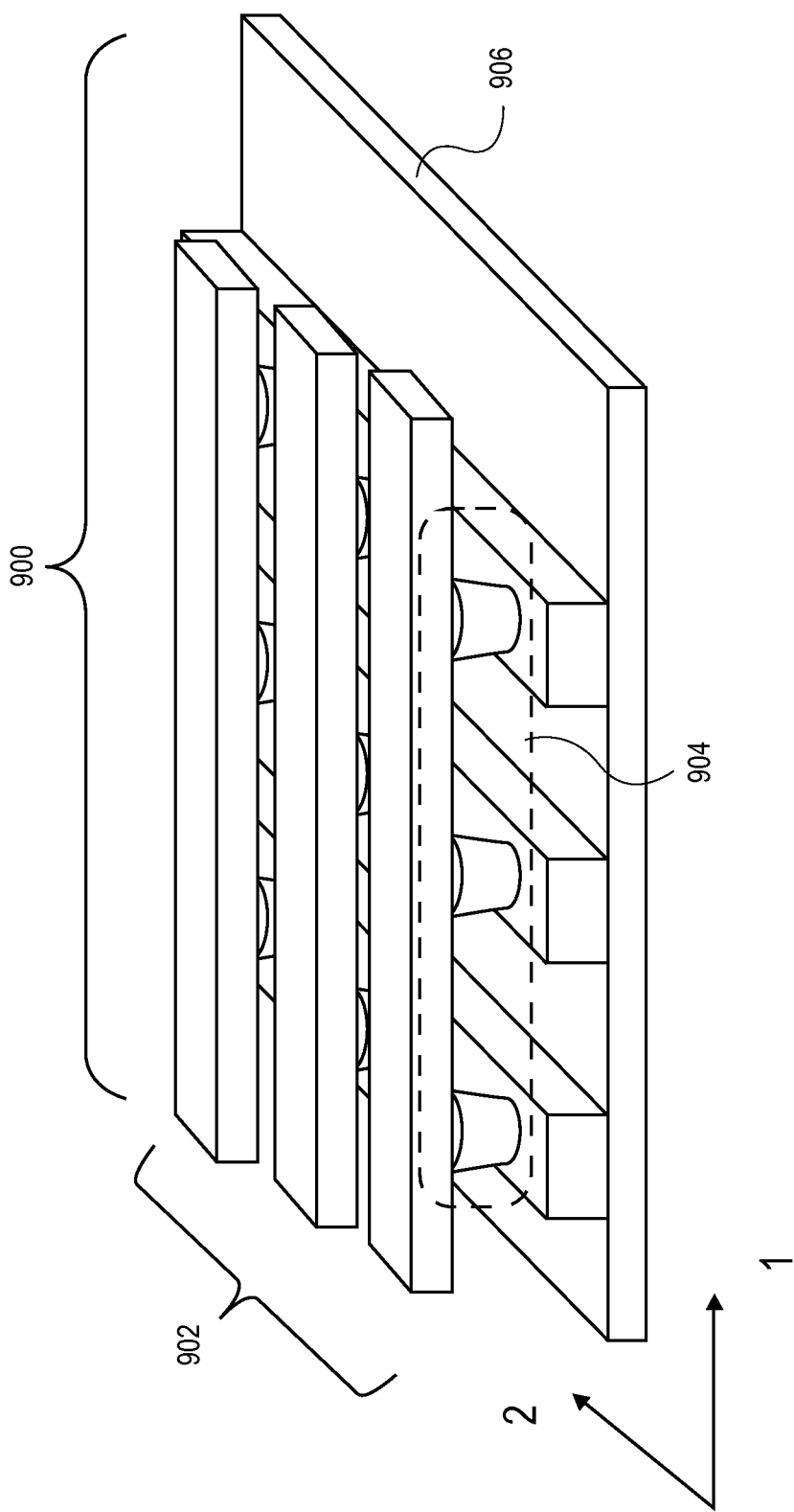
FIG. 9 represents a cross-sectional view of a structure having both a two-dimensional component and a three-dimensional component for modeling in accordance with an embodiment.

FIG. 9 represents a cross-sectional view of a structure having both a two-dimensional component and a three-dimensional component for modeling in accordance with an embodiment. Referring to FIG. 9, a structure 900 has a two-dimensional component 902 and a three-dimensional component 904 above a substrate 906. The grating of the two-dimensional component runs along direction 2, while the grating of the three-dimensional component runs along both directions 1 and 2. In one embodiment, direction 1 is orthogonal to direction 2, as depicted in FIG. 9. In another embodiment, direction 1 is non-orthogonal to direction 2.

In some embodiments, an apparatus, system, or method provides automatic determination of Fourier harmonic order for computation of spectral information for diffraction structures. In some embodiments, the measurement may include diffraction signals from a two- or three-dimensional grating structure generated by an ellipsometric optical metrology system, such as the optical metrology systems 1000 or 1150 described below in association with FIGS. 10 and 11, respectively. However, it is to be understood that the same concepts and principles equally apply to the other optical metrology systems, such as reflectometric systems. The diffraction signals represented may account for features of the two- and three-dimensional grating structure such as, but not limited to, profile, dimension, material composition, or film thickness.

Figure 10:
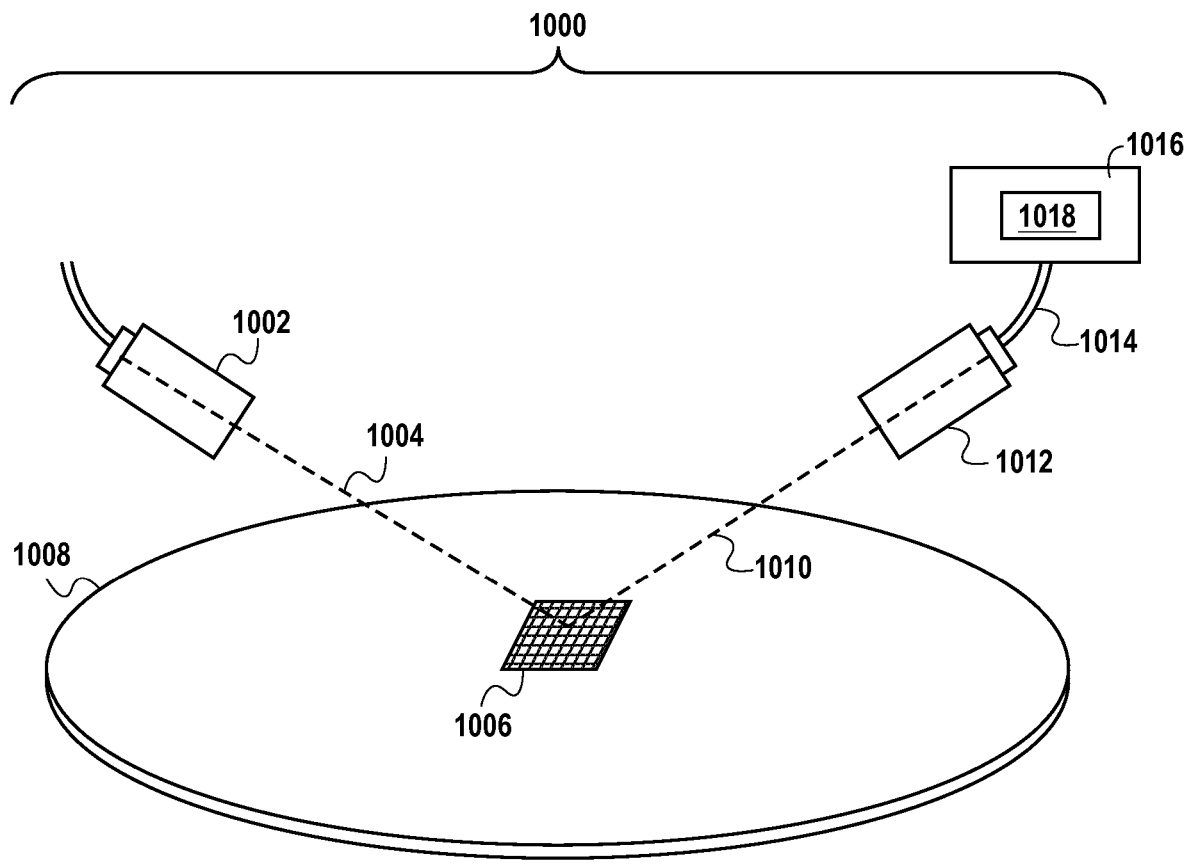
FIG. 10 is an architectural diagram illustrating the utilization of optical metrology to determine parameters of structures on a semiconductor wafer, in accordance with an embodiment.

FIG. 10 is an architectural diagram illustrating the utilization of optical metrology to determine parameters of structures on a semiconductor wafer, in accordance with an embodiment. The optical metrology system 1000 includes a metrology beam source 1002 projecting an incident metrology beam 1004 at the target structure 1006 of a wafer 1008. The incident metrology beam 1004 is projected at an incidence angle θ towards the target structure 1006 (θ is the angle between the incident metrology beam 1004 and a normal to the target structure 1006). The ellipsometer may, in one embodiment, use an incidence angle of approximately 60° to 70°, or may use a lower angle (possibly close to 0° or near-normal incidence) or an angle greater than 70° (grazing incidence). The diffraction beam 1010 is measured by a metrology beam receiver 1012. The diffraction beam data 1014 is transmitted to a profile application server 1016. The profile application server 1016 may compare the measured diffraction beam data 1014 against a library 1018 of simulated diffraction beam data representing varying combinations of critical dimensions of the target structure and resolution.

In one exemplary embodiment, the library 1018 instance best matching the measured diffraction beam data 1014 is selected. It is to be understood that although a library of diffraction spectra or signals and associated hypothetical profiles or other parameters is frequently used to illustrate concepts and principles, embodiments may apply equally to a data space including simulated diffraction signals and associated sets of profile parameters, such as in regression, neural network, and similar methods used for profile extraction. The hypothetical profile and associated critical dimensions of the selected library 1018 instance is assumed to correspond to the actual cross-sectional profile and critical dimensions of the features of the target structure 1006. The optical metrology system 1000 may utilize a reflectometer, an ellipsometer, or other optical metrology device to measure the diffraction beam or signal.

In order to facilitate the description of embodiments, an ellipsometric optical metrology system is used to illustrate the above concepts and principles. It is to be understood that the same concepts and principles apply equally to the other optical metrology systems, such as reflectometric systems. In an embodiment, the optical scatterometry is a technique such as, but not limited to, optical spectroscopic ellipsometry (SE), beam-profile reflectometry (BPR), beam-profile ellipsometry (BPE), and ultra-violet reflectometry (UVR). In a similar manner, a semiconductor wafer may be utilized to illustrate an application of the concept. Again, the methods and processes apply equally to other work pieces that have repeating structures.

Figure 11:
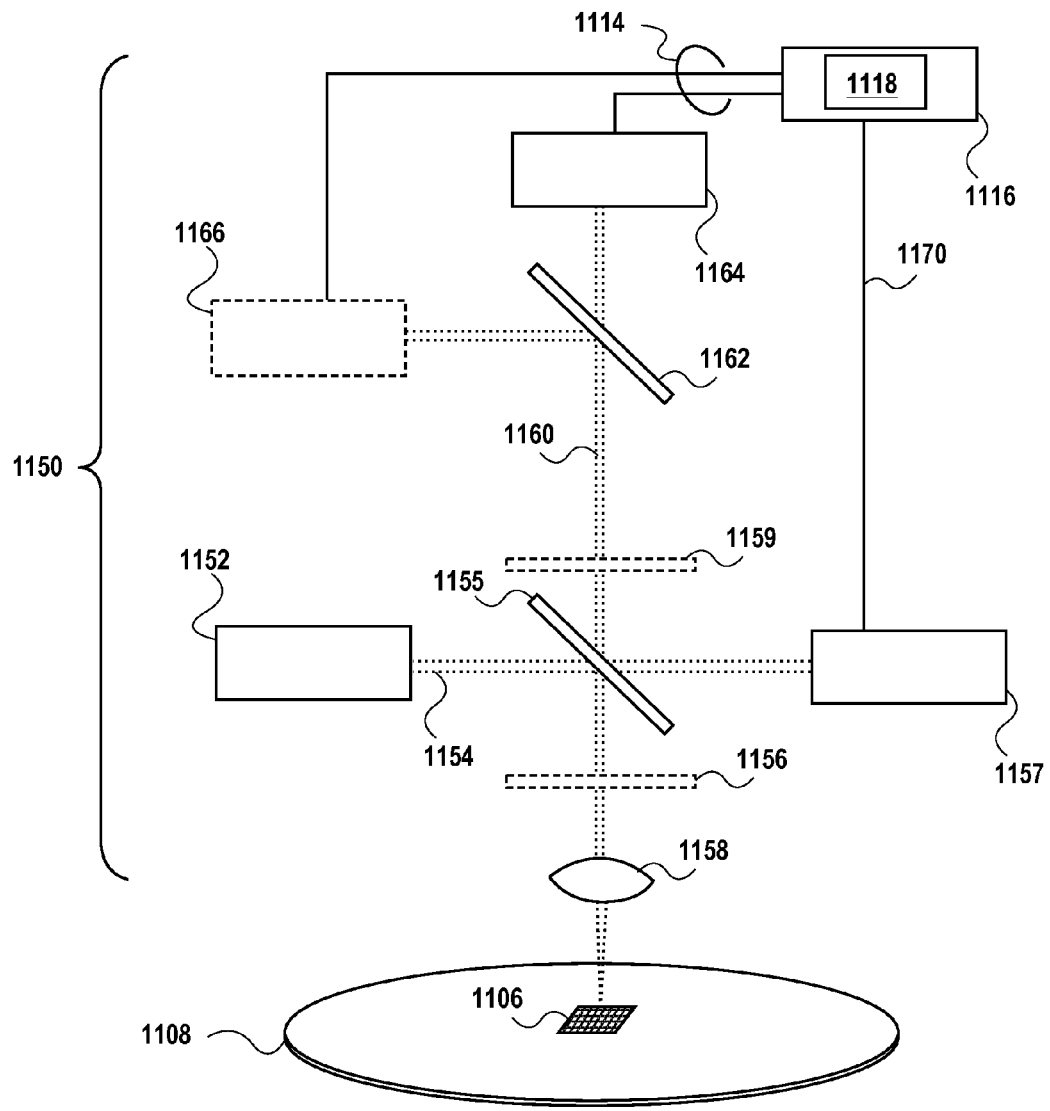
FIG. 11 is an architectural diagram illustrating the utilization of beam-profile reflectometry, beam-profile ellipsometry, or both to determine parameters of structures on a semiconductor wafer in accordance with an embodiment.

FIG. 11 is an architectural diagram illustrating the utilization of beam-profile reflectometry, beam-profile ellipsometry, or both to determine parameters of structures on a semiconductor wafer in accordance with an embodiment. The optical metrology system 1150 includes a metrology beam source 1152 generating a polarized metrology beam 1154. Preferably this metrology beam has a narrow bandwidth of 10 nanometers or less. In some embodiments, the metrology beam source 1152 is capable of outputting beams of different wavelengths by switching filters or by switching between different lasers or super-bright light emitting diodes. Part of this beam is reflected from the beam splitter 1155 and focused onto the target structure 1106 of a wafer 1108 by objective lens 1158, which has a high numerical aperture (NA), preferably an NA of approximately 0.9 or 0.95. The portion of the polarized metrology beam 1154 that is not reflected from the beam splitter is directed to beam intensity monitor 1157. The metrology beam may, optionally, pass through a quarter-wave plate 1156 before the objective lens 1158.

After reflection from the target the reflected beam 1160 passes back through the objective lens and is directed to one or more detectors. If optional quarter-wave plate 1156 is present, the beam will pass back through that quarter-wave plate before being transmitted through the beam splitter 1155. After the beam-splitter, the reflected beam 1160 may optionally pass through a quarter-wave plate at location 1159 as an alternative to location 1156. If the quarter-wave plate is present at location 1156, it will modify both the incident and reflected beams. If it is present at location 1159, it will modify only the reflected beam. In some embodiments, no wave plate may be present at either location, or the wave plate may be switched in and out depending on the measurement to be made. It is to be understood that in some embodiments it might be desirable that the wave plate have a retardance substantially different from a quarter wave, i.e. the retardance value might be substantially greater than, or substantially less than, 90°.

A polarizer or polarizing beam splitter 1162 directs one polarization state of the reflected beam 1160 to detector 1164, and, optionally, directs a different polarization state to an optional second detector 1166. The detectors 1164 and 1166 might be one-dimensional (line) or two-dimensional (array) detectors. Each element of a detector corresponds to a different combination of AOI and azimuthal angles for the corresponding ray reflected from the target. The diffraction beam data 1114 from the detector(s) is transmitted to the profile application server 1116 along with beam intensity data 1170. The profile application server 1116 may compare the measured diffraction beam data 1114 after normalization or correction by the beam intensity data 1170 against a library 1118 of simulated diffraction beam data representing varying combinations of critical dimensions of the target structure and resolution.

For more detailed descriptions of systems that could be used to measure the diffraction beam data or signals for use with embodiments, see U.S. Pat. No. 6,734,967, entitled FOCUSED BEAM SPECTROSCOPIC ELLIPSOMETRY METHOD AND SYSTEM, filed on Feb. 11, 1999, and U.S. Pat. No. 6,278,519 entitled APPARATUS FOR ANALYZING MULTI-LAYER THIN FILM STACKS ON SEMICONDUCTORS, filed Jan. 29, 1998, both of which are incorporated herein by reference in their entirety. These two patents describe metrology systems that may be configured with multiple measurement subsystems, including one or more of a spectroscopic ellipsometer, a single-wavelength ellipsometer, a broadband reflectometer, a DUV reflectometer, a beam-profile reflectometer, and a beam-profile ellipsometer. These measurement subsystems may be used individually, or in combination, to measure the reflected or diffracted beam from films and patterned structures. The signals collected in these measurements may be analyzed to determine parameters of structures on a semiconductor wafer in accordance with embodiments.

Embodiments may be provided as a computer program product, or software, that may include a machine-readable medium having stored thereon instructions, which may be used to program a computer system (or other electronic devices) to perform a process according an embodiment. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 12:
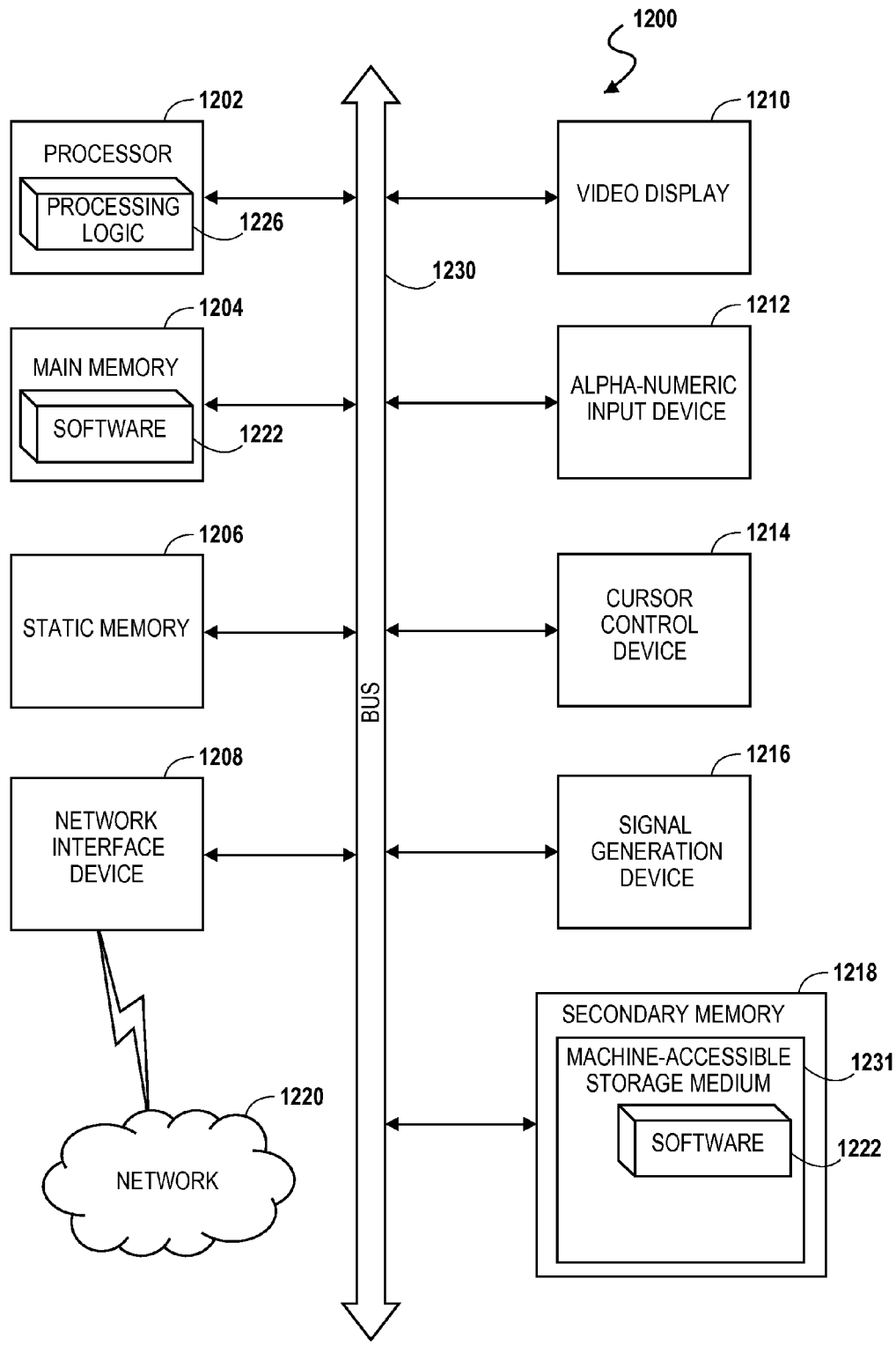
FIG. 12 illustrates a block diagram of a machine in the exemplary form of a computer system in accordance with an embodiment.

FIG. 12 illustrates a block diagram of a machine in the exemplary form of a computer system in accordance with an embodiment within which a set of instructions, for causing the computer to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1200 includes a processor 1202, a main memory 1204 (e.g., read-only memory (ROM), flash memory, dynamic random access memory (DRAM) such as synchronous DRAM (SDRAM) or Rambus DRAM (RDRAM), etc.), a static memory 1206 (e.g., flash memory, static random access memory (SRAM), etc.), and a secondary memory 1218 (e.g., a data storage device), which communicate with each other via a bus 1230. In some embodiments, one or more of the memories are used for storage of data for automatic determination of Fourier harmonic order for computation of spectral information for diffraction structures.

Processor 1202 represents one or more general-purpose processing devices such as a microprocessor, central processing unit, or the like. More particularly, the processor 1202 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1202 may also be one or more special-purpose processing devices such as an application specific integrated circuit (ASIC), a field programmable gate array (FPGA), a digital signal processor (DSP), network processor, or the like. Processor 1202 is configured to execute the processing logic 1226 for performing the operations discussed herein. In some embodiments, processor 1202 provides some or all of the processing for automatic determination of Fourier harmonic order for computation of spectral information for diffraction structures.

The computer system 1200 may further include a network interface device 1208. The computer system 1200 also may include a video display unit 1210 (e.g., a liquid crystal display (LCD) or a cathode ray tube (CRT)), an alphanumeric input device 1212 (e.g., a keyboard), a cursor control device 1214 (e.g., a mouse), and a signal generation device 1216 (e.g., a speaker).

The secondary memory 1218 may include a machine-accessible storage medium (or more specifically a computer-readable storage medium) 1231 on which is stored one or more sets of instructions (e.g., software 1222) embodying any one or more of the methodologies or functions described herein. The software 1222 may also reside, completely or at least partially, within the main memory 1204 and/or within the processor 1202 during execution thereof by the computer system 1200, the main memory 1204 and the processor 1202 also constituting machine-readable storage media. The software 1222 may further be transmitted or received over a network 1220 via the network interface device 1208.

While the machine-accessible storage medium 1231 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

In some embodiments, a machine-accessible storage medium includes instructions stored thereon that cause a data processing system to perform automatic determination of Fourier harmonic order for computation of spectral information for diffraction structures.

It is to be understood that the above methodologies may be applied under a variety of circumstances within the spirit and scope of embodiments. For example, in an embodiment, measurements described above are performed with or without the presence of background light. In an embodiment, a method described above is performed in a semiconductor, solar, light-emitting diode (LED), or a related fabrication process. In an embodiment, a method described above is used in a stand-alone or an integrated metrology tool.

Figure 13:
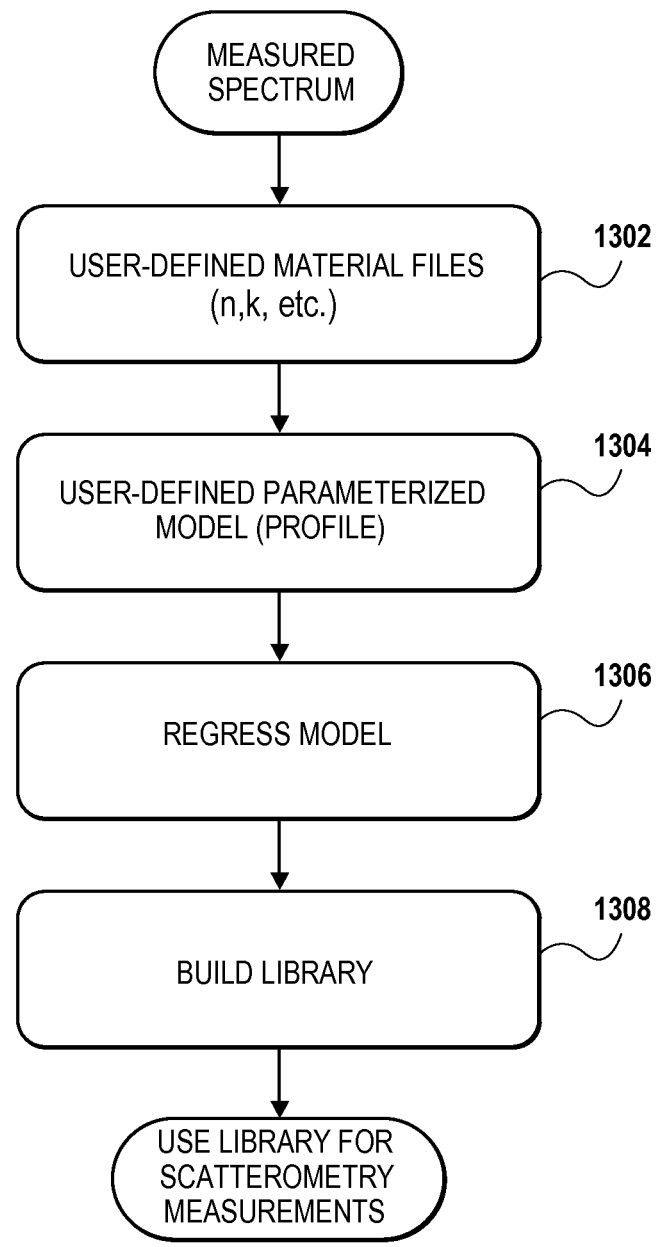
FIG. 13 is a flowchart representing operations in a method for a building parameterized model and a spectral library beginning with sample spectra in accordance with an embodiment.

Analysis of measured spectra generally involves comparing the measured sample spectra to simulated spectra to deduce parameter values of a model that best describe the measured sample. FIG. 13 is a flowchart 1300 representing operations in a method for a building a parameterized model and a spectral library beginning with sample spectra (e.g., originating from one or more work pieces) in accordance with an embodiment.

At operation 1302, a set of material files are defined by a user to specify characteristics (e.g., refractive index or n, k values) of the material(s) from which the measured sample feature is formed.

At operation 1304, a scatterometry user defines a nominal model of the expected sample structure by selecting one or more of the material files to assemble a stack of materials corresponding to those present in the periodic grating features to be measured. Such a user-defined model may be further parameterized through definition of nominal values of model parameters, such as thicknesses, critical dimension (CD), sidewall angle (SWA), height (HT), edge roughness, corner rounding radius, etc. which characterize the shape of the feature being measured. Depending on whether a two-dimensional model (i.e., a profile) or three-dimensional model is defined, it is not uncommon to have 30-50, or more, such model parameters.

From a parameterized model, simulated spectra for a given set of grating parameter values may be computed using rigorous diffraction modeling algorithms, such as Rigorous Coupled Wave Analysis (RCWA). Regression analysis is then performed at operation 1306 until the parameterized model converges on a set of parameter values characterizing a final profile model (for two-dimensional) that corresponds to a simulated spectrum which matches the measured diffraction spectra to a predefined matching criterion. The final profile model associated with the matching simulated diffraction signal is presumed to represent the actual profile of the structure from which the model was generated.

The matching simulated spectra and/or associated optimized profile model can then be utilized at operation 1308 to build a library of simulated diffraction spectra by perturbing the values of the parameterized final profile model. The resulting library of simulated diffraction spectra may then be employed by a scatterometry measurement system operating in a production environment to determine whether subsequently measured grating structures have been fabricated according to specifications. Library generation 1308 may include a machine learning system, such as a neural network, generating simulated spectral information for each of a number of profiles, each profile including a set of one or more modeled profile parameters. In order to generate the library, the machine learning system itself may have to undergo some training based on a training dataset of spectral information. Such training may be computationally intensive and/or may have to be repeated for different models and/or profile parameter domains. Considerable inefficiency in the computational load of generating a library may be introduced by a user's decisions regarding the size of a training dataset. For example, selection of an overly large training dataset may result in unnecessary computations for training while training with a training dataset of insufficient size may necessitate a retraining to generate a library.

For some applications it may be unnecessary to build a library. After the parametric model of the structure has been created and optimized, a regression analysis similar to that described above may be used in real time to determine the best fitting parameter values for each target as the diffraction beam data are collected. If the structure is relatively simple (for example a 2D structure), or if only a small number of parameters need to be measured, regression may be fast enough even though it may be slower than using a library. In other cases, the extra flexibility of using regression may justify some increase in measurement time over using a library. For a more detailed description of methods and systems that are capable of real-time regression of OCD data for use with an embodiment, see U.S. Pat. No. 7,031,848, entitled REAL TIME ANALYSIS OF PERIODIC STRUCTURES ON SEMICONDUCTORS, filed on Jul. 8, 2005, which is incorporated herein by reference in its entirety.

Various embodiments may include various processes. These processes may be performed by hardware components or may be embodied in computer program or machine-executable instructions, which may be used to cause a general-purpose or special-purpose processor or logic circuits programmed with the instructions to perform the processes. Alternatively, the processes may be performed by a combination of hardware and software.

Portions of various embodiments may be provided as a computer program product, which may include a computer-readable medium having stored thereon computer program instructions, which may be used to program a computer (or other electronic devices) for execution by one or more processors to perform a process according to certain embodiments. The computer-readable medium may include, but is not limited to, magnetic disks, optical disks, compact disk read-only memory (CD-ROM), and magneto-optical disks, read-only memory (ROM), random access memory (RAM), erasable programmable read-only memory (EPROM), electrically-erasable programmable read-only memory (EEPROM), magnet or optical cards, flash memory, or other type of computer-readable medium suitable for storing electronic instructions. Moreover, embodiments may also be downloaded as a computer program product, wherein the program may be transferred from a remote computer to a requesting computer.

Many of the methods are described in their most basic form, but processes can be added to or deleted from any of the methods and information can be added or subtracted from any of the described messages without departing from the basic scope of the present embodiments. It will be apparent to those skilled in the art that many further modifications and adaptations can be made. The particular embodiments are not provided to limit the concept but to illustrate it. The scope of the embodiments is not to be determined by the specific examples provided above but only by the claims below.

If it is said that an element "A" is coupled to or with element "B," element A may be directly coupled to element B or be indirectly coupled through, for example, element C. When the specification or claims state that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification indicates that a component, feature, structure, process, or characteristic "may", "might", or "could" be included, that particular component, feature, structure, process, or characteristic is not required to be included. If the specification or claim refers to "a" or "an" element, this does not mean there is only one of the described elements.

An embodiment is an implementation or example. Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. It should be appreciated that in the foregoing description of exemplary embodiments, various features are sometimes grouped together in a single embodiment, figure, or description thereof for the purpose of streamlining the disclosure and aiding in the understanding of one or more of the various novel aspects. This method of disclosure, however, is not to be interpreted as reflecting an intention that the claimed embodiments requires more features than are expressly recited in each claim. Rather, as the following claims reflect, novel aspects lie in less than all features of a single foregoing disclosed embodiment. Thus, the claims are hereby expressly incorporated into this description, with each claim standing on its own as a separate embodiment.

What is claimed is:

1. A method comprising:
   determining, a Fourier harmonic order for computation of spectral information for periodic structures of a target structure, wherein determining the Fourier harmonic order is based at least in part on:
   pitches in each of a plurality of directions of the periodic structures,
   material properties of materials of the periodic structures, and
   characteristics of the periodic structures;
   computing the spectral information for the periodic structures based at least in part on the determined Fourier harmonic order;
   generating a model of the periodic structures for optical metrology measurement utilizing the computed spectral information, wherein the generated model comprises at least one grating structure that runs along at least one direction of the periodic structures and is on top of at least one substrate; and
   performing optical metrology of the target structure with an optical metrology system to measure at least one parameter of the target structure using the generated model of the periodic structures.

2. The method of claim 1, wherein determining the Fourier harmonic order is further based at least in part on interrelationship between any of the pitches, material properties, and characteristics of the periodic structures.

3. The method of claim 1, wherein the characteristics of the periodic structures include one or both of qualitative characteristics and quantitative characteristics.

4. The method of claim 1, wherein computing the spectral information for the periodic structures includes operation of an electromagnetic solver.

5. The method of claim 4, wherein the operation of the electromagnetic solver includes rigorous coupled wave analysis (RCWA).

6. The method of claim 1, wherein the determined Fourier harmonic order is independent of wavelength.

7. The method of claim 1, wherein the determined Fourier harmonic order includes wavelength changing according to a low-order polynomial function.

8. The method of claim 1, wherein the pitches in each of the plurality of directions of the periodic structures include relative dimensions of a unit cell of the periodic structures.

9. The method of claim 1, wherein the characteristics of the periodic structures include one or both of whether a layer of a particular material is a film and whether a structure varies in one or two dimensions.

10. The method of claim 1, wherein the characteristics of the periodic structures include curvature of the periodic structures.

11. The method of claim 1, wherein determining the Fourier harmonic order is further based at least in part on tunable constraints.

12. The method of claim 11, wherein the tunable constraints are set by a user.

13. The method of claim 1, wherein determining the Fourier harmonic order is further based at least in part on a measurement setup for optical metrology measurement of the target structure.

14. The method of claim 13, wherein the measurement setup includes one or more of a spectroscopic or angle-resolved ellipsometer or spectroscopic or angle-resolved reflectometer.

15. The method of claim 1, further comprising identifying each material in a unit cell of the periodic structures in each of an X-direction and a Y-direction.

16. The method of 1, wherein the material properties of materials of the periodic structures include permittivity of each of the materials of the periodic structures.

17. The method of claim 1, wherein the pitches of which the Fourier harmonic order are based on comprise at least a first pitch in a first direction of a first grating structure of the periodic structures and a second pitch in a second direction of a second grating structure of the periodic structures, wherein the first direction is different than the second direction.

18. The method of claim 17, wherein the first grating structure is perpendicular to the second grating structure.

19. The method of claim 1, wherein the Fourier harmonic order is determined without electromagnetic simulation, while the spectral information is computed using electromagnetic simulation.

20. A non-transitory machine-accessible storage medium having instructions stored thereon which when executed cause a data processing system to perform a method automatic determination of Fourier harmonic order for computation of spectral information of diffraction structures, the method comprising:
   determining a Fourier harmonic order for computation of spectral information for periodic diffraction structures of a target structure, wherein the determination of the Fourier harmonic order is based at least in part on:
   pitches in each of a plurality of directions of the periodic structures,
   material properties of materials of the periodic structures, and
   characteristics of the periodic structures;
   computing the spectral information for the periodic structures based at least in part on the determined Fourier harmonic order;
   generating a model of the periodic structures for optical metrology measurement utilizing the computed spectral information, wherein the generated model comprises at least one grating structure that runs along at least one direction of the periodic structures and that is on top of at least one substrate; and
   performing optical metrology of the target structure with an optical metrology system to measure at least one parameter of the target structure using the generated model of the periodic structures.

21. The storage medium of claim 20, wherein determining the Fourier harmonic order is further based at least in part on interrelationship between any of the pitches, material properties, and characteristics of the periodic structures.

22. The storage medium of claim 20, wherein the characteristics of the periodic structures include one or both of qualitative characteristics and quantitative characteristics.

23. The storage medium of claim 20, wherein computing the spectral information for the periodic structures includes operation of an electromagnetic solver.

24. The storage medium of claim 10, wherein the operation of the electromagnetic solver includes rigorous coupled wave analysis (RCWA).

25. A system comprising:
   a processor; and
   memory having instructions stored therein which when executed by the processor cause the system to
      determine a Fourier harmonic order for computation of spectral information for diffraction structures of a target structure, wherein the determination of the Fourier harmonic is based at least in part on:
         pitches in each of a plurality of directions of the periodic structures,
         material properties of materials of the periodic structures, and
         characteristics of the periodic structures; and
   compute the spectral information for the periodic structures based at least in part on the determined Fourier harmonic order,
   generate a model of the periodic structures for optical metrology measurement utilizing the computed spectral information, wherein the generated model comprises at least one grating structure that runs along at least one direction of the periodic structures and that is on top of at least one substrate; and
   perform optical metrology of the target structure with an optical metrology system to measure at least one parameter of the target structure using the generated model of the periodic structures.

26. The system of claim 25, wherein system includes one or more of a spectroscopic or angle-resolved ellipsometer or spectroscopic or angle-resolved reflectometer.

27. The system of claim 25, wherein determining the Fourier harmonic order by the processor is further based at least in part on interrelationship between any of the pitches, material properties, and characteristics of the periodic structures.

28. The system of claim 25, wherein the characteristics of the periodic structures include one or both of qualitative characteristics and quantitative characteristics.

29. The system of claim 25, wherein the periodic structures are microelectronic structures.

* * * * *